United States Patent

Miyazaki et al.

[11] Patent Number: 5,846,730
[45] Date of Patent: Dec. 8, 1998

[54] LABELED COMPLEX

[75] Inventors: Takeshi Miyazaki, Ebina; Kazumi Tanaka; Tsuyoshi Santo, both of Yokohama; Toshikazu Ohnishi, Machida; Tetsuro Fukui, Kawasaki; Tadashi Okamoto, Yokohama, all of Japan

[73] Assignee: Canon Kabushiki Kaisha, Tokyo, Japan

[21] Appl. No.: 888,098

[22] Filed: Jul. 3, 1997

Related U.S. Application Data

[62] Division of Ser. No. 568,680, Dec. 7, 1995, Pat. No. 5,700,647, which is a division of Ser. No. 900,302, Jun. 18, 1992, Pat. No. 5,512,446.

[30] Foreign Application Priority Data

Jun. 21, 1991 [JP] Japan .................................. 3-150428
Oct. 28, 1991 [JP] Japan .................................. 3-281645
Jun. 10, 1992 [JP] Japan .................................. 4-150665

[51] Int. Cl.$^6$ .................................................. C12Q 1/68
[52] U.S. Cl. ............................................. 435/6; 435/72
[58] Field of Search .................................... 435/7.2, 6

[56] References Cited

U.S. PATENT DOCUMENTS

| | | | |
|---|---|---|---|
| 3,770,383 | 11/1973 | Price | 436/509 |
| 3,789,116 | 1/1974 | Kay | 436/800 |
| 4,738,908 | 4/1988 | Oguchi et al. | 430/20 |
| 5,112,960 | 5/1992 | Bronstein et al. | 536/18.1 |
| 5,534,441 | 7/1996 | Miyazaki et al. | 436/517 |

FOREIGN PATENT DOCUMENTS 2191674  7/1990  Japan .

OTHER PUBLICATIONS

K. Sauda et al., "Determination of Protein in Human Serum by High–Performance Liquid Chromatography with Semi-conductor Laser Fluorometric Detection," Analytical Chemistry, vol. 58, No. 13, Nov. 1986, pp. 2649–2653.

Derwent Abstract Accession No. 91–068399/10 (1991).

Smith, et al., Nature, vol. 321 (1986), pp. 674–679.

Mujumdar et al. Cytometry, vol. 10, pp. 11–19 (1989).

Wingrove, Organic Chemistry, pub. by Harper and Row, New York, pp. 163–166, 1981.

*Primary Examiner*—Scott W. Houtteman
*Attorney, Agent, or Firm*—Fitzpatrick, Cella, Harper & Scinto

[57] ABSTRACT

To provide a reagent with excellent stability under storage, which can detect a subject compound to be measured with higher specificity and sensitibity.

Complexes of a compound represented by the general formula (I):

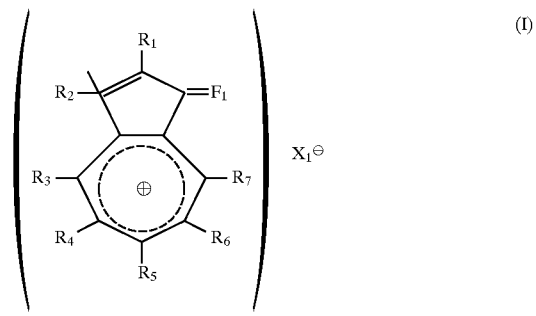

(wherein $R_1$ through $R_7$ independently represent hydrogen atom, halogen atom, alkyl group, aryl group, aralkyl group, sulfonate group, amino group, styryl group, nitro group, hydroxyl group, carboxyl group, cyano group, or aryl azo group; $R_1$ through $R_7$ may or may not be bonded to each other to form a substituted or an unsubstituted condensed ring; $F_1$ represents a divalent organic residue; and $X_1^{\ominus}$ represents an anion) and the like with immunoglobulin and the like are formed.

6 Claims, 1 Drawing Sheet

LABELED COMPLEX

This application is a division of application Ser. No. 08/568,680, filed Dec. 7, 1995, now U.S. Pat. No. 5,700,647, which is a division of application Ser. No. 07/900,302 filed Jun. 18, 1992, U.S. Pat. No. 5,512,446.

BACKGROUND OF THE INVENTION

1. Field of the Invention

The present invention relates to a labeled complex for microassay using near-infrared radiation. More specifically, the present invention relates to a labeled complex capable of specifically detecting a certain particular component in a complex mixture with a higher sensitivity.

2. Related Background Art

On irradiating a laser beam on a trace substance labeled with dyes and the like, information due to the substance is generated such as scattered light, absorption light, fluorescent light and furthermore light acoustics. It is widely known in the field of analysis using lasers, to detect such information so as to practice microassays rapidly with a higher precision.

A gas laser represented by argon laser and helium laser has conventionally been used exclusively as a laser source. In recent years, however semi-conductor laser has been developed, and based on the characteristic features thereof such as inexpensive cost, small scale and easy output control, it is now desired to use the semiconductor laser as a light source.

If diagnostically useful substances from living organisms are assayed by means of the wavelength in ultraviolet and visible regions as has conventionally been used, the background (blank) via the intrinsic fluorescence of naturally occurring products, such as flavin, pyridine coenzyme and serum proteins, which are generally contained in samples, is likely to increase. Only if a light source in a near-infrared region can be used, such background from naturally occurring products can be eliminated so that the sensitivity to substances to be measured might be enhanced, consequently.

However, the oscillation wavelength of a semiconductor laser is generally in red and near-infrared regions (670 to 830 nm), where not too many dyes generate fluorescence via absorption or excitation. A representative example of such dyes is polymethine-type dye having a longer conjugated chain. Examples of labeling substances from living organisms with a polymethine-type dye and using the labeled substances for microanalysis are reported by K. Sauda, T. Imasaka, et al. in the report in Anal. Chem., 58, 2649–2653 (1986), such that plasma protein is labeled with a cyanine dye having a sulfonate group (for example, Indocyanine Green) for the analysis by high-performance liquid chromatography.

Japanese Patent Application Laid-open No. 2-191674 discloses that various cyanine dyes having sulfonic acid groups or sulfonate groups are used for labeling substances from living organisms and for detecting the fluorescence.

However, these known cyanine dyes emitting fluorescence via absorption or excitation in the near-infrared region are generally not particularly stable under light or heat.

If the dyes are used as labeling agents and bonded to substances from living organisms such as antibodies for preparing complexes, the complexes are likely to be oxidized easily by environmental factors such as light, heat, moisture, atmospheric oxygen and the like or to be subjected to modification such as generating cross-links. Particularly in water, a modification such as hydrolysis is further accelerated, disadvantageously. Therefore, the practical use of these complexes as detecting reagents in carrying out the microassay of the components of living organisms has encountered difficulties because of their poor stability under storage.

SUMMARY OF THE INVENTION

The present inventors have made various investigations so as to solve the above problems, and have found that a dye of a particular structure, more specifically a particular polymethine dye, and among others, dye having an azulene skelton, are extremely stable even after the immobilization thereof as a labeling agent onto substances from living organisms. Thus, the inventors have achieved the present invention. It is an object of the present invention to provide a labeled complex with excellent storage stability which can overcome the above problems.

According to an aspect of the present invention, there is provided a labeled complex for detecting a subject compound to be analyzed by means of optical means using near-infrared radiation which complex comprises a substance from a living organism and a labeling agent fixed onto the substance and is bonded to the subject compound to be analyzed, wherein the labeling agent comprises a compound represented by the general formula (I), (II) or (III):

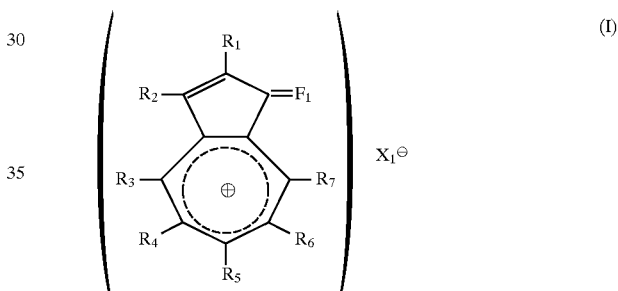

wherein $R_1$ through $R_7$ are independently selected from the group consisting of hydrogen atom, halogen atom, alkyl group, aryl group, aralkyl group, sulfonate group, amino group, styryl group, nitro group, hydroxyl group, carboxyl group, cyano group, or arylazo group; $R_1$ through $R_7$ may be bonded to each other to form a substituted or an unsubstituted condensed ring; $F_1$ represents a divalent organic residue; and $X_1^{\ominus}$ represents an anion;

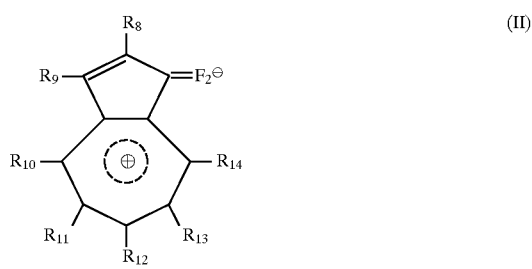

wherein $R_8$ through $R_{14}$ are independently selected from the group consisting of hydrogen atom, halogen atom, alkyl group, aryl group, aralkyl group, sulfonate group, amino group, styryl group, nitro group, hydroxyl group, carboxyl group, cyano group, or arylazo group; $R_8$ through $R_{14}$ may be bonded to each other to form a substituted or an unsubstituted condensed ring; and $F_2$ represents a divalent organic residue;

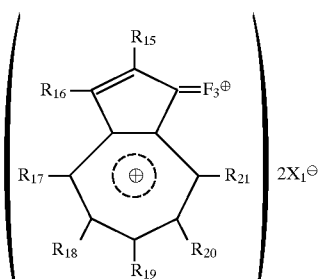

(III)

wherein $R_{15}$ through $R_{21}$ are independently selected from the group consisting of hydrogen atom, halogen atom, alkyl group, aryl group, a substituted or an unsubstituted aralkyl group, a substituted or an unsubstituted amino group, a substituted or an unsubstituted styryl group, nitro group, sulfonate group, hydroxyl group, carboxyl group, cyano group, or arylazo group; $R_{15}$ through $R_{21}$ may or may not be bonded to each other to form a substituted or an unsubstituted condensed ring; $F_3$ represents a divalent organic residue; and $X_1^{\ominus}$ represents an anion.

According to another aspect of the present invention, there is provided a labeled complex for detecting a subject compound to be analyzed by means of optical means using near-infrared radiation which complex comprises a substance from a living organism and a labeling agent fixed onto the substance and is bonded to the subject compound to be analyzed, wherein the labeling agent comprises a compound represented by the general formula (IV):

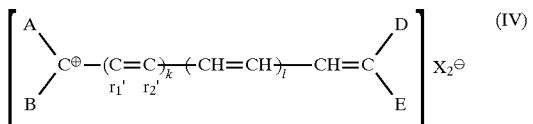

(IV)

wherein A, B, D and E are independently selected from the group consisting of hydrogen atom, a substituted or an unsubstituted alkyl group having two or more carbon atoms, alkenyl group, aralkyl group, aryl group, styryl group and heterocyclic group; $r_1'$ and $r_2'$ are individually selected from the group consisting of hydrogen atom, a substituted or an unsubstituted alkyl group, cyclic alkyl group, alkenyl group, aralkyl group and aryl group; k is 0 or 1; l is 0, 1 or 2; and $X_2^{\ominus}$ represents an anion.

According to another aspect of the present invention, there is provided a method of detecting a subject compound to be analyzed by means of optical means which method comprises using a labeled complex comprised of a substance from a living organism and a labeling agent fixed onto the substance and bonding the complex to the subject compound to be analyzed, wherein the labeling agent comprises a compound represented by the general formula (I), (II) or (III).

According to still another aspect of the present invention, there is provided a method of detecting a subject compound to be analyzed by means of optical means which method comprises using a labeled complex comprised of a substance from a living organism and a labeling agent fixed onto the substance and bonding the complex to the subject compound to be analyzed, wherein the labeling agent comprises a compound represented by the general formula (IV).

DETAILED DESCRIPTION OF THE PREFERRED EMBODIMENTS

Figure 1:
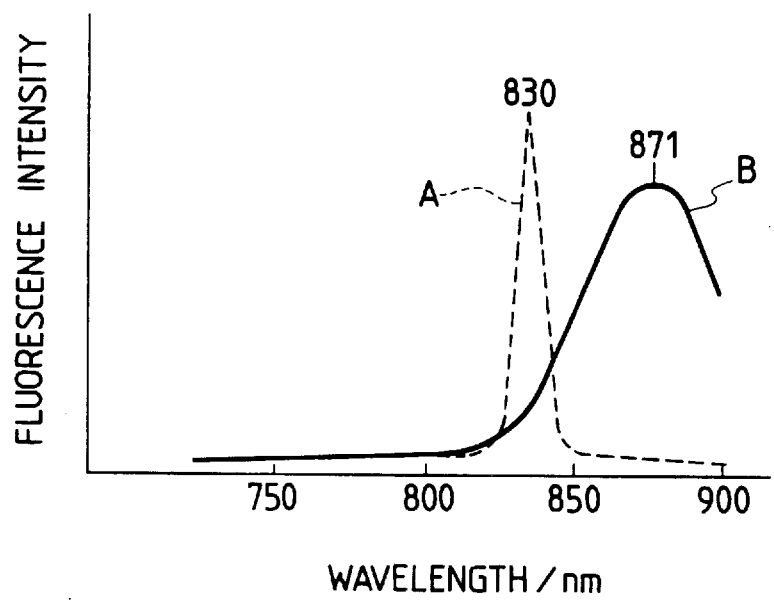
FIG. 1 depicts one example of fluorescence emitting wave form of a labeling agent.

The present invention will now be explained in detail hereinbelow.

In accordance with the present invention, the compound of the general formula (I), (II) or (III) is employed as a labeling agent, wherein $R_1$ to $R_{21}$ individually represent hydrogen atom, halogen atom (chlorine atom, bromine atom, and iodine atom) or a monovalent organic residue, and other such functional groups described above. The monovalent organic residue can be selected from a wide variety of such residues.

The alkyl group is preferably in straight chain or branched chain, having a carbon number of 1 to 12, such as for example methyl group, ethyl group, n-propyl group, iso-propyl group, n-butyl group, sec-butyl group, iso-butyl group, t-butyl group, n-amyl group, t-amyl group, n-hexyl group, n-octyl group, t-octyl group and the like.

The aryl group preferably has a carbon number of 6 to 20, such as for example phenyl group, naphthyl group, methoxyphenyl group, diethylaminophenyl group, dimethylaminophenyl group and the like.

The substituted aralkyl group preferably has a carbon number of 7 to 19, such as for example carboxybenzyl group, sulfobenzyl group, hydroxybenzyl group and the like.

The unsubstituted aralkyl group preferably has a carbon number of 7 to 19, such as for example benzyl group, phenethyl group, α-naphthylmethyl group, β-naphthylmethyl group and the like.

The substituted or unsubstituted amino group preferably has a carbon number of 10 or less, such as for example amino group, dimethylamino group, diethylamino group, dipropylamino group, acetylamino group, benzoylamino group and the like.

The substituted or unsubstituted styryl group preferably has a carbon number of 8 to 14, such as for example styryl group, dimethylaminostyryl group, diethylaminostyryl group, dipropylaminostyryl group, methoxystyryl group, ethoxystyryl group, methylstyryl group and the like.

The aryl azo group preferably has a carbon number of 6 to 14, such as for example phenylazo group, α-napththylazo group, β-naphtylazo group, dimethylaminophenylazo group, chlorophenylazo group, nitrophenylazo group, methoxyphenylazo group and the like.

Of the combinations of $R_1$ and $R_2$, $R_2$ and $R_3$, $R_3$ and $R_4$, $R_4$ and $R_5$, $R_5$ and $R_6$, and $R_6$ and $R_7$ of the general formula (I), at least one combination may form a substituted or an unsubstituted condensed ring. The condensed ring may be five, six or seven membered, including aromatic ring (benzene, naphthalene, chlorobenzene, bromobenzene, methyl benzene, ethyl benzene, methoxybenzene, ethoxybenzene and the like); heterocyclic ring (furan ring, benzofuran ring, pyrrole ring, thiophene ring, pyridine ring, quinoline ring, thiazole ring and the like); and aliphatic ring (dimethylene, trimethylene, tetramethylene and the like). This is the case with the general formulas (II) and (III).

For the general formula (II), at least one combination among the combinations of $R_8$ and $R_9$, $R_9$ and $R_{10}$, $R_{10}$ and $R_{11}$, $R_{11}$ and $R_{12}$, $R_{12}$ and $R_{13}$, and $R_{13}$ and $R_{14}$, may form a substituted or an unsubstituted condensed ring.

Also for the general formula (III), at least one combination of the combinations of $R_{15}$ and $R_{16}$, $R_{16}$ and $R_{17}$, $R_{17}$ and $R_{18}$, $R_{18}$ and $R_{19}$, and $R_{19}$ and $R_{20}$, and $R_{20}$ and $R_{21}$, may form a substituted or an unsubstituted condensed ring.

In the general formulas (I) to (IV) described above, the general formula (I) is specifically preferable; preference is also given individually to hydrogen atom, alkyl group and sulfonate group in the case of $R_1$ to $R_7$; hydrogen atom, alkyl group and sulfonate group in the case of $R_8$ to $R_{14}$; hydrogen atom, alkyl group and sulfonate group in the case of $R_{15}$ to $R_{21}$; alkyl group and aryl group in the case of A, B, D and E; hydrogen atom and alkyl group in the case of $r_1'$ to $r_2'$.

In the general formula (I), $F_1$ represents a divalent organic residue bonded via a double bond. Specific examples of a compound containing such $F_1$ to be used in the present invention, include those represented by the following general formulas (1) to (12), wherein $Q^⊕$ represents the following azulenium salt nucleus and the right side excluding $Q^⊕$ represents $F_1$.

Azulenium salt nucleus ($Q^⊕$)

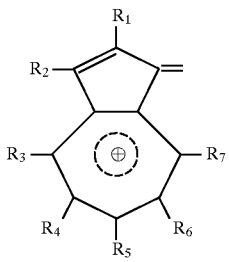

General formula (1)

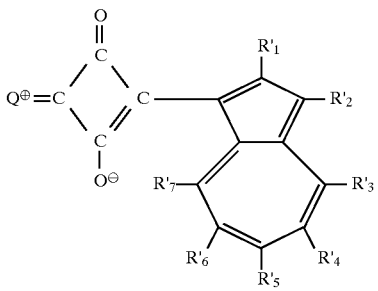

(2)

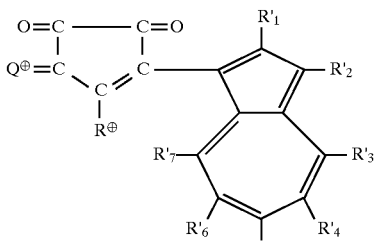

(3)

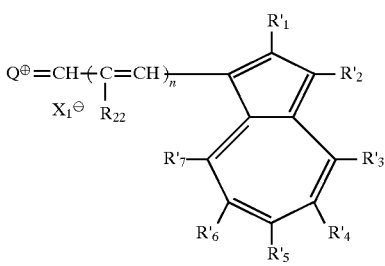

wherein the relation between the azulenium salt nucleus represented by $Q^⊕$ and the azulene salt nucleus on the right side in the formula (3) may be symmetric or asymmetric.

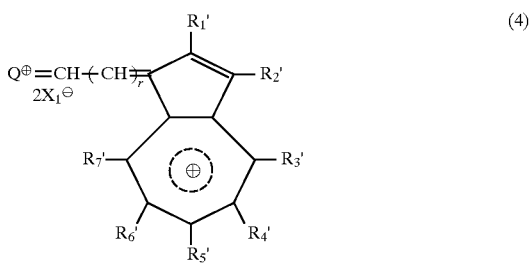

(4)

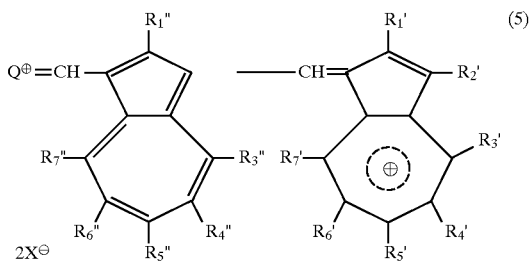

(5)

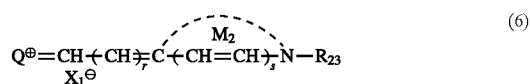

(6)

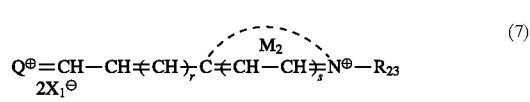

(7)

(8)

(9)

(10)

(11)

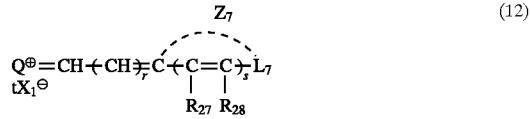

(12)

In the above formulas (1) to (12) as in the case of $R_1$ to $R_7$, $R_1'$ to $R_7'$ and $R_1''$ to $R_7''$ independently represent hydrogen atom, halogen atom, alkyl group, aryl group, aralkyl group, amino group, styryl group, nitro group, hydroxyl group, carboxyl group, cyano group or aryl azo group, while $R_1'$ to $R_7'$ and $R_3''$ to $R_7''$ independently may form a substituted or an unsubstituted condensed ring; n is 0, 1 or 2; r is an integer of 1 to 8; S represents 0 or 1; and t represents 1 or 2.

$M_2$ represents a non-metallic atom group required for the completion of a nitrogen-containing heterocyclic ring.

Specific examples of $M_2$ are atom groups required for the completion of a nitrogen-containing heterocyclic ring, including pyridine, thiazole, benzothiazole, naphthothiazole, oxazole, benzoxazole, naphthoxazole, imidazole, benzimidazole, naphthoimidazole, 2-quinoline, 4-quinoline, isoquinoline or indole, and may be substituted by halogen atom (chlorine atom, bromine atom, iodine atom and the like), alkyl group (methyl, ethyl, propyl, butyl and the like), aryl group (phenyl, tolyl, xylyl and the like), and aralkyl (benzene, p-trimethyl, and the like).

$R_{22}$ represents hydrogen atom, nitro group, sulfonate group, cyano group, alkyl group (methyl, ethyl, propyl, butyl and the like), or aryl group (phenyl, tolyl, xylyl and the like). $R_{23}$ represents alkyl group (methyl, ethyl, propyl, butyl and the like), a substituted alkyl group (2-hydroxyethyl, 2-methoxyethyl, 2-ethoxyethyl, 3-hydroxypropyl, 3-methoxypropyl, 3-ethoxypropyl, 3-chloropropyl, 3-bromopropyl, 3-carboxylpropyl and the like), a cyclic alkyl group (cyclohexyl, cyclopropyl), aryl aralkyl group (benzene, 2-phenylethyl, 3-phenylpropyl, 3-phenylbutyl, 4-phenylbutyl, α-naphthylmethyl, β-naphthylmethyl), a substituted aralkyl group (methylbenzyl, ethylbenzyl, dimethylbenzyl, trimethylbenzyl, chlorobenzyl, bromobenzyl and the like), aryl group (phenyl, tolyl, xylyl, α-naphtyl, β-napthyl) or a substituted aryl group (chlorophenyl, dichlorophenyl, trichlorophenyl, ethylphenyl, methoxydiphenyl, dimethoxyphenyl, aminophenyl, sulfonate phenyl, nitrophenyl, hydroxyphenyl and the like).

$R_{24}$ represents a substituted or an unsubstituted aryl group or the cation group thereof, specifically including a substituted or an unsubstituted aryl group (phenyl, tolyl, xylyl, biphenyl, aminophenyl, α-naphtyl, β-napthyl, anthranyl, pyrenyl, methoxyphenyl, dimethoxyphenyl, trimethoxyphenyl, ethoxyphenyl, diethoxyphenyl, chlorophenyl, dichlorophenyl, trichlorophenyl, bromophenyl, dibromophenyl, tribromophenyl, ethylphenyl, diethylphenyl, nitrophenyl, aminophenyl, dimethylaminophenyl, diethylaminophenyl, dibenzylaminophenyl, dipropylaminophenyl, morpholinophenyl, piperidinylphenyl, piperidinophenyl, diphenylaminophenyl, acetylaminophenyl, benzoylaminophenyl, acetylphenyl, benzoylphenyl, cyanophenyl, sulfonate phenyl, carboxylate phenyl and the like).

$R_{25}$ represents a heterocyclic ring or the cation group thereof, specifically including a monovalent heterocyclic ring derived from cyclic rings, such as furan, thiophene, benzofuran, thionaphthene, dibenzofuran, carbazole, phenothiazine, phenoxazine, pyridine and the like.

$R_{26}$ represents hydrogen atom, alkyl group (methyl, ethyl, propyl, butyl and the like), or a substituted or an unsubstituted aryl group (phenyl, tolyl, xylyl, biphenyl, ethylphenyl, chlorophenyl, methoxyphenyl, ethoxyphenyl, nitrophenyl, aminophenyl, dimethylaminophenyl, diethylaminophenyl, acetylaminophenyl, α-naphthyl, β-naphthyl, anthraryl, pyrenyl, sulfonate phenyl, carboxylate phenyl and the like. In the formula, $Z_7$ represents an atom group required for the completion of pyran, thiapyran, selenapyran, telluropyran, benzopyran, benzothiapyran, benzoselenapyran, benzotelluropyran, naphthopyran, naphthothiapyran, or naphthoselenapyran, or naphtotelluropyran.

$L_7$ represents sulfur atom, oxygen atom or selenium atom or tellurium atom.

$R_{27}$ and $R_{28}$ individually represent hydrogen atom, alkoxy group, a substituted or an unsubstituted aryl group, alkenyl group and a heterocyclic group, More specifically, $R_{27}$ and $R_{28}$ individually represent hydrogen atom, alkyl group (methyl, ethyl, propyl, butyl and the like), alkyl sulfonate group, alkoxyl group (methoxy, ethoxy, propoxy, ethoxyethyl, methoxyethyl and the like), aryl group (phenyl, tolyl, xylyl, sulfonate phenyl, chlorophenyl, biphenyl, methoxyphenyl and the like), a substituted or an unsubstituted styryl group (styryl, p-methylstyryl, o-chlorostyryl, p-methoxystyryl and the like), a substituted or an unsubstituted 4-phenyl, 1,3-butadienyl group (r-phenyl, 1,3-butadienyl, 4-(p-methylphenyl), 1,3-butadienyl and the like), or a substituted or an unsubstituted heterocyclic group (quinolyl, pyridyl, carbazoyl, furyl and the like).

As in the case of $F_1$, the same is true with $F_2$ and $F_3$ of the general formulas (II) and (III), respectively.

Then, in $F_1$, the symbols $R_8'$ to $R_{14}'$ individually correspond to $R_1'$ to $R_7'$; $R_8''$ to $R_{14}''$ individually correspond to $R_1''$ to $R_7''$; in $F_3$, $R_{14}'$ to $R_{21}'$ individually correspond to $R_1'$ to $R_7'$; $R_{14}''$ to $R_{21}''$ individually correspond to $R_1''$ to $R_7''$.

In the azulenium nucleus of the (1) to (12), described above, those represented by the formulas (3), (9) and (10) are more preferably used; and particularly, the formula (3) is preferable.

$R_1$ to $R_{28}$, $R_1'$ to $R_{21}'$ and $R_1''$ to $R_{21}''$ preferably contain one or more well-known polar groups in order to impart water solubility to a compound (labeling agent) represented by the general formula (I), (II) or (III). The polar groups include, for example, hydroxyl group, alkylhydroxyl group, sulfonate group, alkylsulfonate group, carboxylate group, alkylcarboxylate group, tetra-ammonium base and the like. $R_1$ to $R_{28}$, $R_1'$ to $R_{21}'$, and $R_1''$ to $R_{21}''$ preferably contain one or more well-known reactive groups in order that the compound of the general formula (I) can form a covalent bond with a substance from a living organism.

The reactive groups include the reactive sites of isocyanate, isothiocyanate, succinimide ester, sulfosuccinimide ester, imide ester, hydrazine, nitroaryl halide, piperidine disulfide, maleimide, thiophthalimide, acid halide, sulfonyl halide, aziridine, azide nitrophenyl, azide amino, 3-(2-pyridyldithio) propionamide and the like. In these reactive sites, the following spacer groups

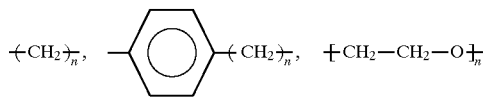

(n=0, 1 to 6) may be interposed in order to prevent steric hindrance during on the bonding of a labeling agent and a substance from a living organism.

Preferable such reactive groups include isothiocyanate, sulfosuccinimide ester, succinimide ester, maleimide and the like. $X_1^{\ominus}$ represents an anion, including chloride ion, bromide ion, iodide ion, perchlorate ion, benzenesulfonate ion, p-toluene sulfonate ion, methylsulfate ion, ethylsulfate ion, propylsulfate ion, tetrafluoroborate ion, tetraphenylborate ion, hexafluorophosphate ion, benzenesulfinic acid salt ion, acetate ion, trifluoroacetate ion, propionate ion, benzoate ion, oxalate ion, succinate ion, malonate ion, oleate ion, stearate ion, citrate ion, monohydrogen diphosphate ion, dihydrogen monophosphate ion, pentachlorostannate ion, chlorosulfonate ion, fluorosulfonate ion, trifluoromethane sulfonate ion, hexafluoroantimoncite ion, molybdate ion, tungstate ion, titanate ion, zirconate ion and the like.

Specific examples of these labeling agents are illustrated in Tables 1, 2 and 3, but are not limited thereto.

The synthetic method of these azulene dyes is described in U.S. Pat. No. 4,738,908.

TABLE 1

| No. | G | F₁ | X₁ | $R_1$ | $R_2$ | $R_3$ | $R_4$ | $R_5$ | $R_6$ | $R_7$ |
|---|---|---|---|---|---|---|---|---|---|---|
| 1 | (I) | (3) $R'_1 = R'_5 = R'_6 = H$<br>$R'_2 = R'_7 = CH_3$<br>$R'_4 = CH(CH_3)_2$, $R'_{22} = H$, $n = 2$ | $BF_4$ | H | H | H | $-(CH_2)_2-C(=O)-O-N$(succinimidyl) | H | H | $CH_3$ |
| 2 | (I) | (3) $R'_1 = R'_2 = R'_6 = H$<br>$R'_3 = R'_7 = CH_3$<br>$R_5 = OCH_3$, $R'_{22} = H$, $n = 2$ | $ClO_4$ | H | H | $CH_3$ | H | $-OCH_3$ | H | $CH_3$ |
| 3 | (I) | (3) $R'_1 = R'_2 = R'_3 = R'_7 = R'_4 = R'_6 = H$<br>$R'_5 = CH_2CH_2CH_2COONa$<br>$R'_{22} = H$ $n = 2$ | I | H | H | $CH_3$ | H | $-CH_2CH_2$<br>$CH_2CH_3$ | H | $CH_3$ |
| 4 | (I) | (3) $R'_1 = R'_2 = R'_3 = R'_4 = R'_6 = R'_7 = H$<br>$R'_5 = C(CH_3)_3$<br>$R'_{22} = H$, $n = 2$ | $ClO_4$ | H | H | H | H | $C(CH_3)_3$ | H | H |
| 5 | (I) | (3) $R'_1 = R'_5 = R'_6 = H$<br>$R'_2$ and $R'_3$ are cyclized<br>with $-(CH_2)_2-$<br>$R'_4 = R'_7 = CH_3$, $R'_{22} = H$, $n = 2$ | $BF_4$ | H | $SO_3^\ominus\,Na^\oplus$ | H | $CH\!\!\left(\!\!\begin{array}{c}CH_3\\CH_3\end{array}\right.$ | H | H | $CH_3$ |
| 6 | (I) | (3) $R'_1 = R'_2 = R'_3 = R'_4 = R'_6 = R'_7 = H$<br>$R'_5 = (CH_2)_3-C(=O)-O-N$(succinimidyl)<br>$R'_{22} = H$, $n = 2$ | $BF_4$ | H | H | H | H | $C(CH_3)_3$ | H | H |

TABLE 1-continued

| No. | G | *G | $F_1$ | $X_1$ | $R_1$ | $R_2$ | $R_3$ | $R_4$ | $R_5$ | $R_6$ | $R_7$ |
|---|---|---|---|---|---|---|---|---|---|---|---|
| 7 | (I) | (3) | $R'_1=R'_2=R'_4=R'_6=H$<br>$R'_3=R'_5=R'_7=CH_3$<br>$R'_{22}=H, n=2$ | 4-CH$_3$-C$_6$H$_4$-SO$_3^-$ | H | H | $CH_3$ | H | $CH_3$ | H | $CH_3$ |
| 8 | (I) | (9) | $r=5$<br>$t=1$<br>$R_{25}=$ (2-methyl-5-SO$_3$Na-benzothiazole with N-C$_2$H$_4$-COONa) | $BF_4$ | H | $CH_3$ | H | H | $R_4$ and $R_5$ are combined to form $-S-CH=C(CH_3)-$ | H | $CH_3$ |
| 9 | (I) | (10) | $r=4$<br>$t=1$<br>$R_{24}=R_{26}=$ 4-(C$_2$H$_5$)$_2$N-C$_6$H$_4$-CH$_3$ | $ClO_4$ | H | $SO_3^\ominus Na^\oplus$ | H | $CH(CH_3)_2$ | H | H | $CH_3$ |
| 10 | (I) | (11) | $r=3$<br>$t=1$<br>$R_{24}=H_2N-$ 4-CH$_3$-C$_6$H$_4$- | $BF_4$ | H | $CH_3$ | H | $CH(CH_3)_2$ | $-(CH_2)_2-C(=O)-O-N$(succinimidyl) | H | $CH_3$ |
| 11 | (I) | (12) | $r=3$ $t=1$ $S=0$<br>$L_7=S$<br>$Z_7=-CH=C(Ph)-CH=C(Ph)-$ | 4-CH$_3$-C$_6$H$_4$-SO$_3^-$ | H | $CH_3$ | H | $CH(CH_3)_2$ | H | H | $CH_3$ |

*G: General Formula

TABLE 2

| No. | G | F₂ | $R_8$ | $R_9$ | $R_{10}$ | $R_{11}$ | $R_{12}$ | $R_{13}$ | $R_{14}$ |
|---|---|---|---|---|---|---|---|---|---|
| 12 | (II) | (1) R'₈ = R'₁₀ = R'₁₂ = R'₁₃ = H<br>R'₉ = R'₁₄ = CH₃<br>R'₁₁ = CH(CH₃)₂ | H | $SO_3^{\ominus} Na^{\oplus}$ | H | CH(CH₃)₂ | H | H | CH₃ |
| 13 | (II) | (1) R'₈ = R'₁₂ = R'₁₃ = R'₁₄ = H<br>R'₁₀ = R'₁₁ =<br>C—S—C=C(CH₃)— | H | CH₃ | —S—CH=C(CH₃)— | | H | H | H |
| 14 | (II) | (2) R'₈ = R'₁₀ = R'₁₂ = R'₁₃ = H<br>R'₉ = R'₁₄ = CH₃<br>R'₁₁ = CH(CH₃)₂ | H | $SO_3^{31} Na^{\oplus}$ | H | CH(CH₃)₂ | H | H | CH₃ |
| 15 | (II) | (2) R'₈ = R'₉ = R'₁₁ = R'₁₃ = H<br>R'₁₀ = R'₁₄ = CH₃<br>R'₁₂ = OC₂H₅ | H | H | CH₃ | H | 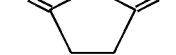 | H | CH₃ |

*G: General Formula

TABLE 3

| No. | G | F$_3$ | X$_1$ | R$_{15}$ | R$_{16}$ | R$_{17}$ | R$_{18}$ | R$_{19}$ | R$_{20}$ | R$_{21}$ |
|---|---|---|---|---|---|---|---|---|---|---|
| 16 | (III) (10) | R$_{24}$ = diethylamino-cyclohexadienylidene; R$_{26}$ = H; r = 1, t = 1 | BF$_4$ | H | CH$_3$ | H | H | formation of —S—CH=C— | H | CH$_3$ |
| 17 | (III) (4) | R'$_{15}$ = R'$_{16}$ = R'$_{18}$ = R'$_{20}$ = H; R'$_{17}$ = R'$_{19}$ = R'$_{21}$ = CH$_3$; r = 1 | I | H | SO$_3^\ominus$ Na$^\oplus$ | H | H | CH$_3$ | H | CH$_3$ |
| 18 | (III) (10) | R'$_{15}$ = R'$_{18}$ = R'$_{20}$ = H; R'$_{16}$ = NO$_2$; R'$_{17}$ = R'$_{19}$ = R'$_{21}$ = CH$_3$; r = 3 | p-CH$_3$-C$_6$H$_4$-SO$_3$ | H | NO$_2$ | CH$_3$ | H | CH$_3$ | H | CH$_3$ |
| 19 | (III) (5) | R'$_{15}$ = R'$_{16}$ = R'$_{17}$ = R'$_{18}$ = H; R'$_{19}$ = R'$_{20}$ = R'$_{21}$ = H; R''$_{15}$ = R''$_{17}$ = R''$_{18}$ = R''$_{19}$ = R''$_{20}$ = R''$_{21}$ = H | ClO$_4$ | H | SO$_3^\ominus$ Na$^\oplus$ | H | H | —(CH$_2$)$_2$—C(=O)—O—N(succinimidyl-SO$_3$Na) | H | H |
| 20 | (III) (8) | R$_{24}$ = (CH$_3$)$_2$N-(4-methylcyclohexadienyl); r = 6, t = 2 | p-CH$_3$-C$_6$H$_4$-SO$_3$ | H | CH$_3$ | H | CH(CH$_3$)$_2$ | H | H | CH$_3$ |

TABLE 3-continued

| No. | G | F₁ | X₁ | R₁ | R₂ | R₃ | R₄ | R₅ | R₆ | R₇ |
|---|---|---|---|---|---|---|---|---|---|---|
| 21 | (III) | (9) benzothiazolium structure with R₂₅=, r=8, t=2, succinimidyl ester substituent | BF₄ | | H | SO₃⁻Na⁺ | H | n-C₈H₁₇ | H | H |
| 22 | (III) | (10) R₂₄=(CH₃OC₂H₄)₂N–C₆H₄–, R₂₆=H₂N–C₆H₄(CH₃)–, r=3, t=2 | p-CH₃-C₆H₄-SO₃⁻ | | H | SO₃⁻Na⁺ | H | CH(CH₃)₂ | H | CH₃ |
| 23 | (III) | (12) R₂₇=H, R₂₈=H₂N–C₆H₄(CH₃)–, Z₇=–CH=C(C₆H₅)–, L₇=T⁺, r=2, S=1, t=2 | I | | H | CH₃ | H | CH(CH₃)₂ | –(CH₂)–CH₂–(maleimidyl) | H | CH₃ |
| 24 | I | (6) R₂₃=C₂H₅, M₂= 3-CH₃-4-SO₃Na-C₆H₃–, r=5, s=0 | I | H | H | H | –(CH₂)₂–C(=O)–O–N(sulfosuccinimidyl, SO₃Na) | H | H | CH₃ |

TABLE 3-continued

| | | | | | | | | | |
|---|---|---|---|---|---|---|---|---|---|
| 25 | I | BF$_4$ | ![structure: r$_{23}$ = -(CH$_2$)$_2$-C(=O)-O-N-ring with C=O; M$_2$ = -S-phenyl-SO$_3$Na with CH$_3$; r = 5, s = 0] | (7) | H | H | H | -CH(CH$_3$)$_2$ | H | CH$_3$ |
| 26 | I | I | R'$_1$ = R'$_3$ = R'$_5$ = R'$_6$ = H<br>R'$_2$ = SO$_3^\ominus$ Na$^\oplus$<br>R$_7$ = CH$_3$ R'$_{22}$ = H<br>R$_4$ = CH(CH$_3$)$_2$<br>n = 2 | (3) | H | H | CH$_3$ | -(CH$_2$)$_3$-N (maleimide ring, O, O) | H | CH$_3$ |
| 27 | I | BF$_4$ | R'$_1$ = R'$_3$ = R'$_4$ = R'$_6$ = R'$_7$ = H<br>R'$_2$ = SO$_3^\ominus$ Na$^\oplus$<br>R'$_5$ = (CH$_2$)$_3$-COO$^\ominus$ Na$^\oplus$ | (3) | H | SO$_3^\ominus$ Na$^\oplus$ | H | -(CH$_2$)$_3$-C(=O)-O-N (succinimide with SO$_3^\ominus$Na$^\oplus$) | H | H |

*G: General Formula

These illustrated labeling agents absorb light in a near-infrared wavelength region of 670 to 900 nm, and the molar absorption coefficient ε is in the region of 50,000 to 300,000 l/mol·cm. The illustrated labeling agents include those generating strong fluorescence.

Table 4 shows the maximum absorption wavelength (λmax) and maximum fluorescence wavelength of (λem) each of the labeling agents generating fluorescence in the region of the semiconductor laser wavelength (medium: ethanol/dichloromethane=¼).

TABLE 4

| No. | Maximum absorption wavelength (λ max) | Maximum fluorescence wavelength (λ em) |
|---|---|---|
| 2 | 828 | 863 |
| 3 | 833 | 871 |
| 4 | 825 | 857 |
| 6 | 825 | 851 |
| 7 | 830 | 871 |
| 16 | 790 | 828 |
| 27 | 826 | 870 |

FIG. 1 shows the fluorescence emitting wave form on the incidence of semiconductor laser beam (10 mW) of 830 nm into a labeling agent No. 3. The apparatus for measurement is IMUC-7000 manufactured by Otsuka Electron Co., Ltd.

In FIG. 1, curve A shows incident wave form of semiconductor laser beam. Curve B shows a fluorescence emitting wave form of a labeling agent No. 3.

Alternatively, the labeling agent to be used in the present invention is a compound of the general formula (IV), wherein A, B, D and E individually represent hydrogen atom or alkyl group (for example, ethyl group, n-propyl group, iso-propyl group, n-butyl group, sec-butyl group, iso-butyl group, t-butyl group, n-amyl group, t-amyl group, n-hexyl group, n-octyl group, t-octyl group and the like); and additionally, other alkyl groups such as for example a substituted alkyl group (for example, 2-hydroxyethyl group, 3-hydroxypropyl group, 4-hydroxybutyl group, 2-acetoxyethyl group, carboxymethyl group, 2-carboxyethyl group, 3-carboxypropyl group, 2-sulfoethyl group, 3-sulfopropyl group, 4-sulfobutyl group, 3-sulfate propyl group, 4-sulfate butyl group, N-(methylsulfonyl)-carbamylmethyl group, 3-(acetylsulfamyl)propyl group, 4-(acetylsulfamyl)butyl group and the like); cyclic alkyl groups (for example cyclohexyl group), allyl group ($CH_2=CH-CH_2-$), alkenyl group (vinyl group, propenyl group, butenyl group, pentenyl group, hexenyl group, heptenyl group, octenyl group, dodecyl group, prenyl group and the like), aralkyl group (for example, benzyl group, phenethyl group, α-naphthylmethyl group, β-naphthylmethyl group and the like), a substituted aralkyl group (for example, carboxybenzyl group, sulfobenzyl group, hydroxybenzyl group and the like), a substituted or an unsubstituted aryl group (for example, phenyl group, aminophenyl group, naphthyl group, tolyl group, xylyl group, methoxyphenyl group, dimethoxyphenyl group, trimethoxyphenyl group, ethoxyphenyl group, dimethylaminophenyl group, diethylaminophenyl group, dipropylaminophenyl group, dibenzylaminophenyl group, diphenylaminophenyl group, sulfonate phenyl group, carboxylate phenyl group and the like), a substituted or an unsubstituted heterocyclic group (for example, pyridyl group, quinolyl group, lepidyl group, methylpyridyl group, furyl group, phenyl group, indolyl group, pyrrole group, carbazolyl group, N-ethylcarbazolyl group and the like), or a substituted or an unsubstituted styryl group (for example, styryl group, methoxystyryl group, dimethoxystyryl group, trimethoxystyryl group, ethoxystyryl group, aminostyryl group, dimethylaminostyryl group, diethylaminostyryl group, dipropylaminostyryl group, dibenzylaminostyryl group, diphenylaminostyryl group, 2,2-diphenylvinyl group, 2-phenyl-2-methylvinyl group, 2-(dimethylaminophenyl)-2-phenylvinyl group, 2-(diethylaminophenyl)-2-phenylvinyl group, 2-(dibenzylaminophenyl)-2-phenylvinyl group, 2,2-di(diethylaminophenyl)vinyl group, 2,2-di(methoxyphenyl)vinyl group, 2,2-di(ethoxylphenyl)vinyl group, 2-(dimethylaminophenyl)-2-methylvinyl group, 2-(diethylaminophenyl)-2-ethylvinyl group, and the like).

$r_1'$ and $r_2'$ individually represent hydrogen atom or alkyl group (for example, methyl group, ethyl group, n-propyl group, iso-propyl group, n-butyl group, sec-butyl group, iso-butyl group, t-butyl group, n-amyl group, t-amyl group, n-hexyl group, n-octyl group, t-octyl group and the like); and additionally, other alkyl groups such as for example a substituted alkyl group (for example, 2-hydroxyethyl group, 3-hydroxypropyl group, 4-hydroxybutyl group, 2-acetoxyethyl group, carboxymethyl group, 2-carboxyethyl group, 3-carboxypropyl group, 2-sulfoethyl group, 3-sulfopropyl group, 4-sulfobutyl group, 3-sulfate propyl group, 4-sulfate butyl group, N-(methylsulfonyl)-carbamylmethyl group, 3-(acetylsulfamyl)propyl group, 4-(acetylsulfamyl)butyl group and the like); cyclic alkyl group (for example, cyclohexyl group), allyl group ($CH_2=CH-CH_2-$), alkenyl group (vinyl group, propenyl group, butenyl group, pentenyl group, hexenyl group, heptenyl group, octenyl group, dodecyl group, prenyl group and the like), aralkyl group (for example, benzyl group, phenethyl group, α-naphthylmethyl group, β-naphthylmethyl group and the like), and a substituted aralkyl group (for example, carboxybenzyl group, sulfobenzyl group, hydroxybenzyl group and the like).

A, B, D, $r_1'$ and $r_2'$ preferably contain one or more well-known polar groups in order to impart water solubility to the labeling agent (dye) of the general formula (IV). The reactive group includes for example hydroxyl group, alkylhydroxyl group, sulfone group, alkyl sulfone group, carboxyl group, alkylcarboxyl group, tetra-ammonium base and the like. A, B, D, $r_1'$ and $r_2'$ preferably contain one or more well-known reactive groups in order that the labeling agent of the general formula (IV) can form a covalent bond with a substance from a living organism.

The reactive group includes the reactive sites of isocyanate, isothiocyanate, succinimide ester, sulfosuccinimide ester, imide ester, hydrazine, nitroaryl halide, piperidine disulfide, maleimide, thiophthal imide, acid halide, sulfonyl halide, aziridine, azide nitrophenyl, azide amino, 3-(2-pyridyldithio) propionamide and the like. In these reactive sites, the following spacer groups

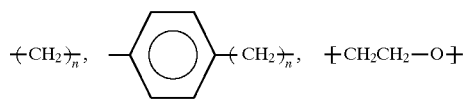

(n=0, 1 to 16) may be interposed in order to prevent the steric hindrance on the bonding of a labeling agent and a substance from a living organism.

Preferable such reactive groups include isothiocyanate, sulfosuccinimide ester, succinimide ester, maleimide and the like.

The k in the general formula (IV) is 0 or 1 and l is 1 or 2.

$X_2^{\ominus}$ represents an anion, including chlorine ion, bromine ion, iodine ion, perchlorate ion, benzenesulfonate ion, p-toluene sulfonate ion, methylsulfate ion, ethylsulfate ion, propylsulfate ion, tetrafluoroborate ion, tetraphenylborate ion, hexafluorophosphate ion, benzenesulfinic acid ion, acetate ion, trifluoroacetate ion, propionate ion, benzoate ion, oxalate ion, succinate ion, malonate ion, oleate ion, stearate ion, citrate ion, monohydrogen diphosphate ion, dihydrogen monophosphate ion, pentachlorostannate ion, chlorosulfonate ion, fluorosulfonate ion, trifluoromethane sulfonate ion, hexafluoroantimonate ion, molybdate ion, tungstate ion, titanate ion, zirconate ion and the like.

Specific examples of these labeling agents are illustrated in Table 5, but are not limited thereto.

TABLE 5

| No | A | B | D | E | $r_1'$ $r_2'$ | $X_2$ | |
|----|---|---|---|---|---|---|---|
| 28 | ph | | | (phenyl)-H$_2$N | — — | BF$_4$ | k = 0, l = 1 |
| 29 | (CH$_3$)$_2$N-phenyl | ↓ | ↓ | (phenyl)-H$_2$N | — — | BF$_4$ | k = 0, l = 1 |
| 30 | (CH$_3$)$_2$N-phenyl | Me-phenyl | (CH$_3$)$_2$—N— | Me-phenyl | — — | I | k = 0, l = 1 gleaming |
| 31 | (C$_2$H$_5$)$_2$N-phenyl | H$_2$N-phenyl | (C$_2$H$_5$)$_2$N— | H$_2$N-phenyl | H CH$_3$— | AsF$_6$ | k = 1, l = 0 |
| 32 | (C$_2$H$_5$)$_2$N-phenyl | ↓ | ↓ | NaOOC-phenyl | — — | FSO$_3$ | k = 0, l = 1 |
| 33 | (C$_2$H$_5$)$_2$N-phenyl | C$_2$H$_5$O-phenyl | (C$_2$H$_5$)$_2$N-phenyl | C$_2$H$_5$O-phenyl | — — | CH$_3$-phenyl-SO$_5$ | k = 0, l = 1 |
| 34 | (C$_2$H$_5$)$_2$N-phenyl | Ph | (C$_2$H$_5$)$_2$N-phenyl | NaOOC-phenyl | — — | CH$_3$-phenyl-SO$_5$ | k = 0, l = 1 |
| 35 | (C$_2$H$_5$)$_2$N-phenyl | ↓ | ↓ | ↓ | H NaOOC-phenyl | BF$_4$ | k = 1, l = 0 |

TABLE 5-continued

| No | A | B | D | E | $r_1'$ $r_2'$ | $X_2$ | |
|---|---|---|---|---|---|---|---|
| 36 | (C₂H₅)₂N–C₆H₄– | H | (C₂H₅)₂N–C₆H₄–CH=CH– | ↓ | — | AsF₆ | k = 0, l = 0 |
| 37 | (C₂H₅)₂N–C₆H₄– | ↓ | ↓ | ↓ | H, H₂N–C₆H₄– (NH₂) | BF₄ | k = 1, l = 0 |
| 38 | pyrrolidinyl–C₆H₄– | ↓ | (C₂H₅)₂N–C₆H₄– | ↓ | — | FSO₃ | k = 0, l = 1 |
| 39 | (C₂H₅)₂N–C₆H₄– | ↓ | ↓ | ↓ | H, –C₂H₅ | BF₄ | k = 1, l = 0 |
| 40 | (C₂H₅)₂N–C₆H₄– | ↓ | ↓ | H₂N–C₆H₄– | — | BF₄ | k = 0, l = 1 |
| 41 | (C₂H₅)₂N–C₆H₄– | ↓ | ↓ | ↓ | H, NaO₃S–C₆H₄– | BF₄ | k = 1, l = 0 |
| 42 | (CH₃)₂N–C₆H₄– | CH₃– | (CH₃)₂N–C₆H₄– | CH₃– | H, CH₃ | FSO₃ | k = 1, l = 0 |
| 43 | (CH₃)₂N–C₆H₄– | C₃H₇– | (CH₃)₂N–C₆H₄– | C₃H₇– | H, H₂N–C₆H₄– | BF₄ | k = 1, l = 0 |

TABLE 5-continued
| No | A | B | D | E | $r_1'$ $r_2'$ | $X_2$ | |
|----|---|---|---|---|---|---|---|
| 44 |  |  |  |  | — |  | k = 0, l = 1 |
| 45 |  |  |  |  | — | $AsF_6$ | k = 0, l = 1 |
| 46 |  |  |  |  |  | I | k = 0, l = 1 |
| 47 |  |  |  |  |  | I | k = 1, l = 0 |
| 48 |  |  |  |  | — | $BF_4$ | k = 0, l = 1 |

These illustrated labeling agents absorb light in a near-infrared wavelength region of 670 to 900 nm, and the molar absorption coefficient ε is in the region of 50,000 to 300,000 l/mol·cm. Some of the illustrated labeling agents generate intense fluorescence.

The dye No. 30 illustrated in Table 5 exhibits the maximum absorption at a wavelength of 819 nm in a near-infrared region and emits fluorescence. The maximum fluorescence wavelength (λem) is 864 nm (medium; dichloromethane).

In accordance with the present invention, the labeling agents described above are immobilized onto a substance from a living organism, but the substance from a living organism to be immobilized is selectively determined based on a substance to be analyzed or a subject sample. That is, if a substance is selected from a living organism having a biological specificity to a subject sample, the substance to be analyzed can be detected with specificity. By the term "substance from a living organism" is meant naturally occurring or synthetic peptides, proteins, enzymes, sugars, rectins, viruses, bacteria, nucleic acids, DNA, RNA, antigens (including for example recombinant antigens), antibodies and the like. The substances specifically useful in terms of clinical pathology include the following; immunoglobulin such as IgG, IgM, IgE and the like; plasma proteins and antibodies thereof, such as compliments, CRP, ferritin, α1-microglobulin, β2-microglobulin, and the like; tumor markers and antibodies thereof, such as α-fetoprotein, carcinoembryonic antigen (CEA), prostate acid phosphatase (PAP), CA19-9, CA-125 and the like; hormones and antibodies thereof such as luteinizing hormone (LH), follicle stimulating hormone (FSH), human chorionic gonadotropin (hCG), estrogen, insulin and the like; substances in relation with virus infection and antibodies thereof, such as HBV-related antigens (HBs, HBe, HBc), HIV, ATL and the like; bacteria and antibodies thereof, such as *Corynebacterium diphteriae, Clostridium botulinum*, mycoplasma, *Treponema pallidum* and the like; protozoae and antibodies thereof such as *Toxoplasma gondii*, Trichomonas, Leishmania, Tripanozoma, malaria protozoa and the like; pharmaceutical agents and antibodies thereof, such as antileptic agents including phenytoin, phenobarbital and the like, cardiovascular agents including quinidine and digoxin, antasthmatic agents including theophylline, antibiotics including chloramphenicol and gentamycin; as well as enzymes, enterotoxin (streptolysin O) and the antibodies thereof. Depending on the type of sample, a substance which can incur the antigen-antibody reaction with a substance to be measured in a sample is appropriately selected for use.

In accordance with the present invention, the following known method can be utilized in order to immobilize a labeling agent onto a substance from a living organism such as a physiological active substance.

There are illustrated for example i) ion bonding method, ii) physical absorption method, iii) covalent bonding method and the like.

The ion bonding method comprises electrostatically bonding a labelling agent having principally a positive charge to a substance from a living organism such as proteins, DNA, RNA and the like.

The physical absorption method comprises utilizing the hydrophobic bond between the lipophilic part of a labeling agent and the lipophilic part of a protein.

The reaction process of bonding is simple in accordance with the ion bonding method and physical absorption method, but the bonding strength of a labeling agent and a substance from a living organism is weak.

On contrast, the covalent bonding method comprises bonding a highly reactive functional group to at least one of a labeling agent and a substance from a living organism, and covalently bonding the two through the functional group whereby a highly intense bonding strength can be generated. In bonding a labeling agent with a substance from a living organism such as physiological active substances via covalent bonds, the functional groups being present in the substance from a living organism and which can be involved in the bonding, include free amino group, hydroxyl group, phosphate group, carboxyl group, the sulfhydryl group of cysteine, the imidazole group of histidine, phenol group of tyrosine, the hydroxyl group of serine and threonine, and the like.

These functional groups react with a variety of diazonium salts, acid amides, isocyanate, active-type halogenated alkyl groups, active-type ester groups and the like. Therefore, by a variety of methods, dyes can be immobilized onto a substance from a living organism by introducing these functional groups into a labeling agent. Alternatively, the conformation of a substance from a living organism, specifically that of proteins, is readily damaged because it is retained through relatively weak bonds such as hydrogen bond, hydrophobic bond, ion bond and the like. Thus, the immobilization with a labeling agent preferably should be carried out under mild conditions, without processing by means of high temperatures, strong acids and strong alkalis.

One method of carrying out the immobilization under mild conditions includes the use of bifunctional cross-linking agents which react with a labeling agent and with the functional groups of a substance from a living organism. The bifunctional cross-linking agents include, for example, carbodiimide represented by the general formula R—N═C═N—R', dialdehyde represented by the general formula CHO—R—CHO, diisocyanate represented by O═C═N—R—N═C═O (wherein R and R' represent individually the same or a different substituted or unsubstituted alkyl group, aryl group alkylaryl group or aryl alkyl group), and the like.

The analysis of a certain particular objective substance is conducted by using the resulting labeled complex in which a labeling agent is immobilized onto a substance from a living organism.

If a target (analytical subject) is one species of cell, the labeled complex is bonded to a specific substance on the cell complimentary to the substance from a living organism bonded to the labeled complex via a specific bonding such as an antigen-antibody reaction or, the hydrogen bonding between nucleic acids. Then, the amount of such antigen, antibody or nucleic acids can be measured based on the fluorescence or absorbance of the system.

If the analysis is effected of a target in relation with an antigen and an antibody, a complex bonded through the labeling agent to an antigen (or an antibody) and an antibody (an antigen if a labeling agent is immobilized onto the antibody) to be measured are subjected to antigen-antibody reaction. The complex (B; bonded type) bonded to the antibody (antigen) is then separated from the complex (F; free type) which is not bonded to the antibody (antiger) (B/F separation). Thereafter, the amount of the complex (B) is determined based on the fluorescence or absorbance. The technique utilizing the antigen-antibody reaction described above is described in details in "Examination and Technology", Vol. 16, No. 7 (1988).

In terms of detection sensitivity, furthermore, it is preferable that two or more, preferably 10 or more labeling agents are bonded to one molecule of a substance from a living organism. In terms of synthesis and sensitivity, preferably 10 to 100, more preferably 20 to 50 such agents may be bonded to one molecule thereof.

The present invention will now be explained with reference to examples.

EXAMPLE 1

Anti-human CRP sheep serum (IgG fraction; manufactured by Cooper Biomedical Inc.) was diluted with phosphate buffer, pH 8.0, to a concentration of 0.5 mg/ml, to prepare an antibody solution. To 8 ml of the antibody solution were added 0.2 mg of a labeling agent No. 3 of Table 1 ($\lambda$max=833 nm) and 0.09 g of 1-ethyl-3-(3-dimethylaminopropyl)-carbodiimide hydrochloride (referred to as WSC hereinafter) (manufactured by Dojin Chemicals, Co. Ltd.) for reaction at room temperature for three hours, to generate a labeling agent-antibody complex. The labeling agent-antibody complex was separated and purified from unreacted substances by gel filtration chromatography on a column packed with Sepharose 6B. The bonding molar ratio of the labeling agent and the antibody in the complex thus obtained was 2.1:1. By using a spectrophotometer Shimadzu UV-3100S, the absorbance of the complex was measured at wavelengths $\lambda$=833 nm and $\lambda$=280 nm, separately, to calculate the molar ratio of the labeling agent and the antibody.

EXAMPLE 2

Rectin·Concanavalin A (manufactured by E. Y. Laboratories Co. Ltd.) was diluted with phosphate buffer, pH 8.2, to a concentration of 0.2 mg/ml, to prepare a rectin solution.

With 10 ml of the rectin solution was reacted 0.2 mg of a labeling agent No. 6 of Table 1 ($\lambda$max=825 nm) at room temperature for three hours. The labeling agent-rectin complex was separated and purified on a gel filtration chromatocolumn packed with Sepharose 6B. The molar ratio of the labeling agent and the rectin in the complex obtained was 3.7:1. The absorbances at wavelengths $\lambda$=825 and $\lambda$=280 nm were measured by a spectrophotometer Shimadzu UV-3100S, to calculate the molar ratio of the labeling agent and the rectin.

EXAMPLE 3

Anti-human HCG monoclonal antibody (manufactured by ZyMED Lab. Inc.) was diluted with phosphate buffered physiological saline (PBS), pH 7.2, to a concentration of 0.2 mg/ml, to prepare a monoclonal antibody solution.

To 8 ml of the antibody solution was added 0.3 mg of a labeling agent No. 12 of Table 1 ($\lambda$max=705 nm) for agitation at room temperature for three hours. The labeling agent-antibody complex was separated and purified by gel filtration chromatography on a column packed with Sepharose 6B.

The molar ratio of the labeling agent and the antibody in the labeling agent-antibody complex thus obtained was 1.7:1. By using a spectrophotometer Shimadzu UV-3100S, the absorbance of the complex was measured at wavelengths $\lambda$=705 nm and $\lambda$=280 nm, separately, to calculate the molar ratio of the labeling agent and the antibody.

EXAMPLE 4

M13mp18 single-strand DNA (7249 bases) (manufactured by TAKARA Liquor KK.) (0.1 mg) was diluted with 5 mmol phosphate buffer, pH 6, to prepare a DNA solution. A labeling agent No. 5 (0.1 mg) shown in Table 1 ($\lambda$max=796 nm) was dissolved in 5 ml of distilled water, and subsequently, 5 ml of the DNA solution was gradually added dropwise to the resulting dye solution. Agitation was further effected at room temperature for 2 hours, to produce a DNA-labeling agent complex.

To the solution of the DNA-labeling agent complex described above was added further 40 ml of ethanol, to precipitate the DNA-labeling agent complex. The DNA-labeling agent complex was separated on a filter, followed by washing with ethanol. The DNA-labeling agent complex after the washing was again dissolved in 2 ml of the phosphate buffer, pH 6. The amount of the labeling agent bonded to that of the DNA was 0.5 $\mu$g per $\mu$g·DNA. The absorbance of the complex was measured at wavelengths $\lambda$=705 nm and $\lambda$=280 nm, separately, to calculate the concentrations of the labeling agent and the DNA.

EXAMPLE 5

A 20-mer oligonucleotide having a base sequence partially complimentary to the base sequence of a model target nucleic acid M13mp18 ss DNA was synthesized by a DNA synthesizer 381 A, manufactured by ABI Co. Ltd. Then, a primary amine was introduced into the 5' terminus of the oligonucleotide by using a N-MMT-hexanol amine linker manufactured by Milligen Co. Ltd., instead of general amidide reagents. A predetermined protocol was followed to perform cutting out from the CPG-support, deprotection (including the deprotection of monomethoxytrityl group as a protective group of the primary amine), and the purification by high-performance liquid chromatography.

After mixing together 200 $\mu$g of the oligonucleotide, 100 $\mu$l of 1M sodium carbonate buffer, pH 9.0, and 700 $\mu$l of water, 2 mg of a labeling agent No. 27 ($\lambda$max=826 nm) shown in Table 1, which had preliminarily been dissolved in 200 $\mu$l of dimethyl formamide, was gradually added under agitation. After the reaction at room temperature for 24 hours, the peak of the nucleic acid was decreased on a high-performance liquid chromatogram, whereas a new peak having the absorbances of the nucleic acid and the labeling agent developed. Thus, the reaction solution was nearly purified on a gel filtration column, NAP-50, manufactured by Pharmacia, which was then purified by HPLC to obtain 175 $\mu$g of the nucleic acid-labeling agent complex.

Comparative Example 1

The chemical structure of a well-known cyanine-type near-infrared absorption dye NK-1967 (manufactured by Nippon Photosensitive Dye Research Institute) is depicted hereinbelow.

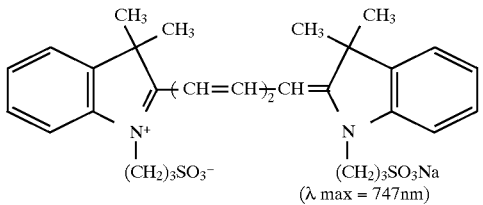

($\lambda$ max = 747nm)

To 5 ml of the antibody solution prepared in Example 1 was added 0.3 mg of the cyanine dye, and agitated at room temperature for 3 hours, to generate a labeling agent-antibody complex.

The labeling agent-antibody complex was separated and purified by gel filtration chromatography on a column packed with Sepharose 6B.

The molar ratio of the labeling agent and the antibody was 1.7:1. The absorbances at wavelength $\mu$=747 nm and $\mu$=280 nm were measured by a spectrophotometer Shimadzu UV-3100S to calculate the molar ratio of the labeling agent and the antibody.

Complex stability under storage

In order to examine the complex stability under storage, the following experiments were carried out.

The labeled complexes prepared in Examples 1 to 5 and Comparative Example 1 were prepared to predetermined concentrations with 10 mmol phosphate buffer, pH 7.2. The solutions of the labeled complexes were kept in dark at 7° C. for three days. At the initiation and termination of the test of complex stability under storage, the absorbance was measured at predetermined wavelengths to calculate the ratio of the absorbance at the termination, provided that the absorbance at the initiation was designated as 100.

For the complexes exhibiting fluorescence, the ratio of the fluorescence intensity at the termination was calculated, provided that the fluorescence intensity at the initiation was designated as 100.

The results are shown in Table 6.

TABLE 6

Stability under storage of labeled complexes

| Example | Concentration | Change in absorbance* (wavelength in nm) | Change in fluorescence intensity** (wavelength in nm) |
| --- | --- | --- | --- |
| 1 | 0.4 g/ml | 93.4 (833) | 94 (875) |
| 2 | 0.4 g/ml | 91.9 (825) | 90 (870) |
| 3 | 0.5 g/ml | 94.2 (705) | — |
| 4 | 0.4 g/ml | 95.1 (796) | — |
| 5 | 0.5 g/ml | 96.1 (826) | 93 (870) |
| Comparative Example 1 | 0.5 g/ml | 71.2 (747) | 63 (820) |

*The initial absorbance was designated as 100.
**The initial fluorescence was designated as 100.

As is shown in Table 6, the labeled complexes of the present invention showed lower change of the absorbance or fluorescence intensity in water than those of Comparative Example.

EXAMPLE 6

Anti-human CRP sheep serum (IgG fraction; manufactured by Cooper Biomedical Inc.) was diluted with PBS, pH 7.2, to a concentration of 0.5 mg/ml, to prepare an antibody solution. To 8 ml of the antibody solution were added 0.2 mg of a labeling agent No. 29 of Table 5 ($\lambda$max=819 nm) and 0.09 g of WSC for reaction at room temperature for three hous, to generate a dye-antibody complex. The dye-antibody complex was separated and purified from unreacted substances by gel filtration chromatography on a column packed with Sepharose 6B. The molar ratio of the dye and the antibody in the complex thus obtained was 2.5:1. By using a spectrophotometer, Shimadzu UV-3100S, the absorbance of the complex was measured at wavelength $\lambda$=819 nm and $\lambda$=280 nm, separately, to calculate the molar ratio of the dye and the antibody.

EXAMPLE 7

Anti-human HCG monoclonal antibody (manufactured by ZyMED Lab, Inc.) was diluted with PBS to a concentration of 0.4 mg/ml, to prepare a monoclonal antibody solution. To 2 ml of the monoclonal antibody solution were added 0.3 mg of a dye No. 32 of Table 5 ($\lambda$max=825 nm) and 0.10 g of Woodward reagent (manufactured by Tokyo Chemicals, Co. Ltd.) for reaction at room temperature for three hours. The dye-antibody complex was separated and purified by gel filtration chromatography on a column packed with Sepharose 6B. The molar ratio of the dye and the antibody in the dye-antibody complex thus obtained was 3.1:1. By using a spectrophotometer Shimadzu UV-3100S, the absorbance of the complex was measured at wavelengths $\lambda$=825 nm and $\lambda$=280 nm, separately, to calculate the molar ratio of the dye and the antibody.

EXAMPLE 8

Rectin·Concanavalin A (manufactured by E. Y. Laboratories Co. Ltd.) was diluted with PBS to a concentration of 0.2 mg/ml, to prepare a rectin solution. With 10 ml of the rectin solution were added 0.2 mg of a dye No. 40 of Table 5 ($\lambda$max=805 nm) and 10 ml of 0.05M sodium borate buffer, pH 8.0 containing 1% glutaraldehyde at room temperature for one hour. The dye-rectin complex was separated and purified on a gel filtration chromatocolumn packed with Sepharose 6B. The molar ratio of the dye and the rectin in the complex obtained was 1.7:1. The absorbances at wavelengths $\lambda$=805 and $\lambda$=280 nm were measured by a spectrophotometer Shimadzu UV-3100S, to calculate the molar ratio of the dye and the rectin.

EXAMPLE 9

M13mp18 single-strand DNA (7249 bases) (manufactured by TAKARA Liquor KK.) (0.1 mg) was diluted with 5 mmol phosphate buffer, pH 6, to prepare a DNA solution. A dye No. 35 (0.1 mg) shown in Table 5 ($\lambda$max=780 nm) was dissolved in 2 ml of ethanol, followed by gradual dropwise addition of 5 ml of the DNA solution to the resulting dye solution under stirring. Agitation was further effected at room temperature for 2 hours, to produce a DNA-dye complex.

To the solution of the DNA-dye complex described above was added further 40 ml of ethanol, to precipitate the DNA-dye complex. The DNA-dye complex was separated on a filter, followed by washing several times with ethanol. The DNA-dye complex after the washing was again dissolved in 2 ml of the phosphate buffer, pH 6. The amount of the dye bonded to that of the DNA was 0.5 $\mu$g per $\mu$g·DNA. The absorbance of the complex was measured at wavelengths $\lambda$=780 nm and $\lambda$=260 nm, separately, to calculate the concentrations of the dye and the DNA.

EXAMPLE 10

A 20-mer oligonucleotide having a base sequence partially complimentary to the base sequence of a model target nucleic acid M13mp18 ss DNA was synthesized by a DNA synthesizer 381 A, manufactured by ABI Co. Ltd. Then, a primary amine was introduced into the 5' terminus of the oligonucleotide by using a N-MMT-hexanol amine linker manufactured by Milligen Co. Ltd., instead of general amidide reagents. A predetermined protocol was followed to perform cutting out from the CPG-support, deprotection (including the deprotection of monomethoxytrityl group as a protective group of the primary amine), and the purification by high-performance liquid chromatography.

After mixing together 200 $\mu$g of the oligonucleotide, 100 $\mu$l of 1M sodium carbonate buffer, pH 9.0, and 700 $\mu$l of water, 2 mg of a dye No. 46 ($\lambda$max=810 nm) shown in Table 5, which had preliminarily been dissolved in 200 $\mu$l of dimethyl formamide, was gradually added under agitation. After the reaction at room temperature for 24 hours, the peak of the nucelic acid was decreased on a high-performance liquid chromatogram, whereas a new peak having the absorbances of the nucleic acid and the dye developed. Thus, the reaction solution was nearly purified on a gel filtration column, NAP-50, manufactured by Pharmacia, which was then purified by HPLC to obtain 175 μg of the nucleic acid-dye complex.

Complex stability under storage

In order to examine the stability under storage of dye complexes, the following experiments were carried out.

The labeled dye complexes prepared in Examples 6 to 10 were prepared to predetermined concentrations with 10 mmol phosphate buffer, pH 7.2. The solutions of the labeled complexes were kept in dark at 7° C. for three days. At the initiation and termination of the test of complex stability under storage, the absorbance was measured at predetermined wavelengths. Then, the ratio of the absorbance at the termination was calculated, provided that the absorbance at the initiation was designated as 100.

The results are shown in Table 7.

TABLE 7

Stability under storage of labeled dye complexes

| Example | Concentration | Wavelength for measurement | Change in absorbance (initial absorbance was designated as 100) |
|---|---|---|---|
| 6 | 0.5 g/ml | 819 | 95.1 |
| 7 | 0.5 g/ml | 825 | 94.5 |
| 8 | 0.5 g/ml | 805 | 91.3 |
| 9 | 0.4 g/ml | 780 | 95.7 |
| 10 | 0.4 g/ml | 810 | 93.9 |

As is shown in Table 7, the labeled dye complexes of the present invention showed lower change of the absorbance in water than those of Comparative Example.

EXAMPLE 11

A 20-mer oligonucleotide having a base sequence partially complimentary to the base sequence of a model target nucleic acid M13mp18 ss DNA was synthesized by a DNA synthesizer 381 A, manufactured by ABI Co. Ltd. Then, by using a deoxyuridylic acid derivative monomer:

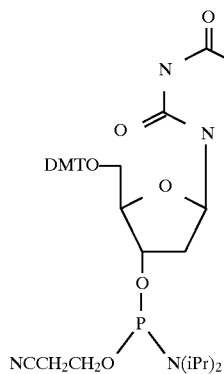

with an amino group introduced, instedad of general amidide reagents, 20 such deoxyuridylic acid derivatives each having a primary amine group were added to the 5' terminus of the oligonucleotide. Routine method was followed to perform cutting out from the CPG-support, deprotection (including the deprotection of trifluoroacetyl group as a protective group of the primary amine), and the purification by high-performance liquid chromatography.

After mixing together 200 μg of the oligonucleotide bonding the primary amines, 100 μl of 1M sodium carbonate buffer, pH 9.0, and 700 μl of water, 5 mg of a dye No. 27 (λmax=826 nm) shown in Table 1, which had preliminarily been dissolved in 200 μl of dimethyl formamide, was gradually added under agitation. After the reaction at 40° C. for 24 hours, the peak of the nucleic acid was decreased on a high-performance liquid chromatogram, whereas a new peak having the absorbances of the nucleic acid and the labeling agent developed. Thus, the reaction solution was nearly purified on a gel filtration column, NAP-50, manufactured by Pharmacia, which was then purified by HPLC to obtain 350 μg of the nucleic acid-labeling agent complex. The absorbance of the nucleic acid-labeling agent complex at 826 nm had the intensity about 20-fold that of the nucleic acid-labeling agent shown in Example 5.

In accordance with the present invention, a stable complex can be formed with less decomposition of dyes, and hence with less change in absorbance or with less change in fluorescence, by bonding a labeling agent of a particular structure to a substance from a living organism.

Therefore, the complex of the present invention can provide a reagent with excellent stability under storage for the application to microanalysis.

What is claimed is:

1. A method of detecting a subject compound to be analyzed by means of optical means which method comprises using a labeled complex comprised of a substance from a living organism and a labeling agent fixed onto the substance and bonding the complex to the subject compound to be analyzed, wherein the labeling agent comprises a compound represented by the general formula (I), (II) or (III):

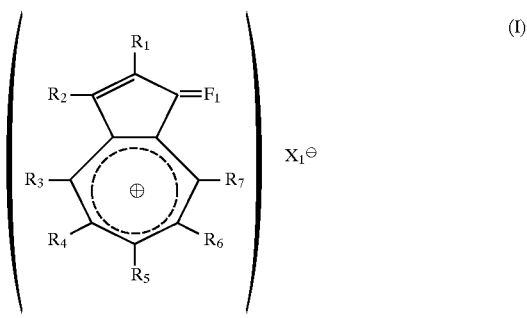

wherein $R_1$ through $R_7$ are independently selected from the group consisting of hydrogen, halogen, alkyl, aryl, aralkyl, sulfonate, amino, styryl, nitro, hydroxyl, carboxyl, cyano, and arylazo;

$R_1$ through $R_7$ may be bonded to each other to form a substituted or an unsubstituted condensed ring;

$F_1$ represents a divalent organic residue; and
$X_1^\ominus$ represents an anion;

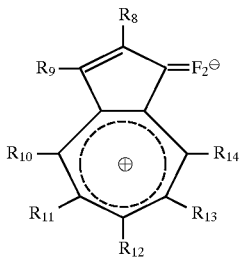 (II)

wherein $R_8$ through $R_{14}$ are independently selected from the group consisting of hydrogen, halogen, alkyl, aryl, aralkyl, sulfonate, amino, styryl, nitro, hydroxyl, carboxyl, cyano, and arylazo;

$R_8$ through $R_{14}$ may be bonded to each other to form a substituted or an unsubstituted condensed ring; and $F_2$ represents an anionic divalent organic residue

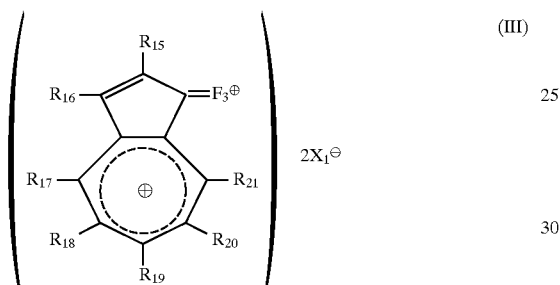 (III)

wherein $R_{15}$ through $R_{21}$ are independently selected from the group consisting of hydrogen, halogen, alkyl, aryl, a substituted or an unsubstituted aralkyl, a substituted or an unsubstituted amino, a substituted or an unsubstituted styryl, nitro, sulfonate, hydroxyl, carboxyl, cyano, and arylazo;

$R_{15}$ through $R_{21}$ may or may not be bonded to each other to form a substituted or an unsubstituted condensed ring;

$F_3$ represents a cationic divalent organic residue; and $X_1^\ominus$ represents an anion.

2. The method according to claim 1, wherein the substance from a living organism is an antibody or an antigen.

3. The method according to claim 1, wherein the substance from a living organism is a nucleic acid.

4. The analyzing method according to any one of claims 1 to 3, wherein the optical means is an optical means using near-infrared ray.

5. The method according to claim 1, wherein $F_2^\ominus$ is represented by the following general formula (1) or (2):

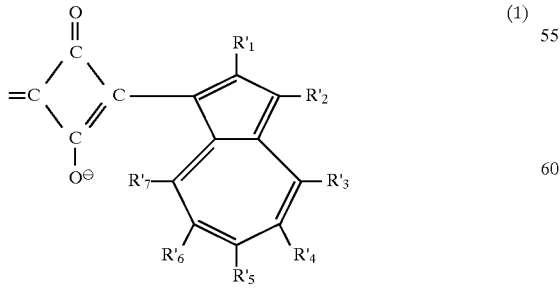 (1)

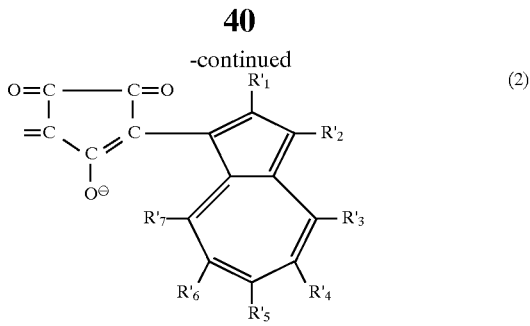 (2)

wherein $R_1'$ to $R_7'$ are each hydrogen, halogen, alkyl, aryl, aralkyl, amino, styryl, nitro, hydroxyl, carboxyl, cyano or aryl azo and combinations of $R_1'$ to $R_7'$ may form substituted or unsubstituted condensed rings, said combinations being formed by $R_1'$ and $R_2'$, $R_2'$ and $R_3'$, $R_3'$ and $R_4'$, $R_4'$ and $R_5'$, $R_5'$ and $R_6'$ or $R_6'$ and $R_7'$.

6. The method according to claim 1 wherein $F_3^\oplus$ is represented by the following general formula (4), (5), (8) or (9):

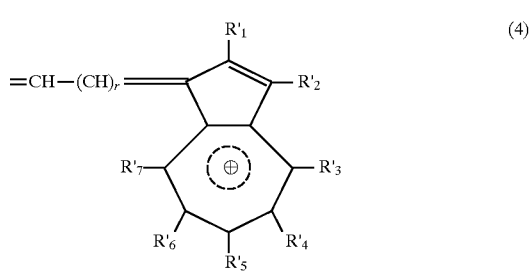

wherein in formulas (4), (5), (8) and (9) $R_1'$ to $R_7'$ and $R_1''$ to $R_7''$ are each hydrogen, halogen, alkyl, aryl, aralkyl, amino, styryl, nitro, hydroxyl, carboxyl, cyano or aryl azo and combinations of $R_1'$ to $R_7'$ and $R_1''$ to $R_7''$ may form substituted or unsubstituted condensed rings, said combinations being formed by $R_1'$ and $R_2'$, $R_2'$ and $R_3'$, $R_3'$ and $R_4'$, $R_5'$ and $R_6'$, $R_6'$ and $R_7'$, $R_3''$ and $R_4''$, $R_4''$ and $R_5''$, $R_5''$ and $R_6''$ or $R_6''$ and $R_7''$.

* * * * *

UNITED STATES PATENT AND TRADEMARK OFFICE
CERTIFICATE OF CORRECTION

PATENT NO. : 5,846,730

DATED : December 8, 1998

INVENTOR(S): TAKESHI MIYAZAKI ET AL.   Page 1 of 5

It is certified that error appears in the above-identified patent and that said Letters Patent is hereby corrected as shown below:

ON THE COVER PAGE AT [56] REFERENCES CITED, FOREIGN PATENT DOCUMENTS

"2191674   7/1990   Japan" should read
--2-191674  7/1990 Japan--.

ON COVER PAGE AT [57], ABSTRACT

Line 5, "sensitibity." should read --sensitivity.--.

COLUMN 1

Line 24, "argon" should read --an argon--;
Line 24, "hilium" should read --a helium--;
Line 26, "however" should read --however, a--.

COLUMN 2

Line 13, "dye" (2nd occurence) should read --a dye --.
Line 31, "F$_1$" should read --R--;
Line 46, "F$_1$" should read --R--;
Line 50, "F$_2$" should read --R$_A$--;
Line 66, "F$_2$" should read --R$_A$--.

COLUMN 3

Line 4, "F$_3$" should read --R$_B$--;
Line 20, "F$_3$" should read --R$_B$--.

UNITED STATES PATENT AND TRADEMARK OFFICE
CERTIFICATE OF CORRECTION

PATENT NO. : 5,846,730

DATED : December 8, 1998

INVENTOR(S): TAKESHI MIYAZAKI ET AL.

It is certified that error appears in the above-identified patent and that said Letters Patent is hereby corrected as shown below:

COLUMN 4

Line 38, "α-napththylazo" should read --α-naphthylazo--;
Line 39, "β-naphtylazo  should read --β-naphthylazo --.

COLUMN 5

Line 5, "$F_1$" should read --R--;
Line 7, "$F_1$" should read --R--;
Line 12, "$F_1$." should read --R--.

COLUMN 6

Lines 14-15, " 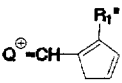 " should read -- 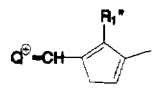 --.

COLUMN 7

Line 12, "β-napthyl)" should read --β-naphthyl)--;
Line 20, "β-napthyl)" should read --β-naphthyl)--;
Line 49, "naphtotelluropyran." should read
  --naphthotelluropyran.--.

UNITED STATES PATENT AND TRADEMARK OFFICE
CERTIFICATE OF CORRECTION

PATENT NO. : 5,846,730

DATED : December 8, 1998

INVENTOR(S): TAKESHI MIYAZAKI ET AL.

It is certified that error appears in the above-identified patent and that said Letters Patent is hereby corrected as shown below:

COLUMN 8

Line 7, "$F_1$," should read --R,--; and "$F_2$ and $F_3$" should read --$R_A$ and $R_B$--;
Line 9, "$F_1$," should read --R,--;

Line 11, "$F_3$," should read --$R_B$,--;
Line 41, "on" should be deleted--.

COLUMNS 9-10, TABLE 1

In col. 3, "$F_1$" should read --R--; "$R'_1 = R'_5 = R'_6 = H$" should read --$R'_1 = R'_3 = R'_5 = R'_6 = H$--.

COLUMNS 11-12, TABLE 1

In col. 3, "$F_1$" should read --R--.

COLUMNS 13-14, TABLE 2

In Col. 7, "5$CH(CH_3)_2$" should read --$CH(CH_3)_2$--; "10$CH(CH_3)_2$" should read --$CH(CH_3)_2$-- and "15" should be deleted.

COLUMNS 15-16, TABLE 3

"$F_3$" should read --$R_B$--.

UNITED STATES PATENT AND TRADEMARK OFFICE
CERTIFICATE OF CORRECTION

PATENT NO. : 5,846,730

DATED : December 8, 1998

INVENTOR(S): TAKESHI MIYAZAKI ET AL.

It is certified that error appears in the above-identified patent and that said Letters Patent is hereby corrected as shown below:

COLUMNS 17-18, TABLE 3

"$F_1$" should read --R--.

COLUMN 31

Line 40, "Trichomonas, Leishma-" should be italicized;
Line 41, "nia ›Tripanozoma," should be italicized.

COLUMN 32

Line 50, "or," should read --or--;
Line 62, "(antiger)" should read --(antigen)--.

COLUMN 35

Line 53, "hous," should read --hours,--.

COLUMN 38

Line 20, "intensity" should read --intensity of--.

UNITED STATES PATENT AND TRADEMARK OFFICE
CERTIFICATE OF CORRECTION

PATENT NO. : 5,846,730

DATED : December 8, 1998

INVENTOR(S): TAKESHI MIYAZAKI ET AL.          Page 5 of 5

It is certified that error appears in the above-identified patent and that said Letters Patent is hereby corrected as shown below:

<u>COLUMN 40</u>

Line 19, "claim 1" should read --claim 1,--.

Signed and Sealed this

Thirty-first Day of October, 2000

Attest:

Q. TODD DICKINSON

*Attesting Officer*          *Director of Patents and Trademarks*